United States Patent [19]

Zhdanova et al.

[11] 4,054,489
[45] Oct. 18, 1977

[54] METHOD OF PREPARING L-GLUTAMIC ACID AND ITS SODIUM SALT

[76] Inventors: Nelli Isaakovna Zhdanova, Leningradskoe shosse, 112/1, korpus 3, kv. 748; Lev Mikhailovich Evstjugov-Babaev, ulitsa Pushkina, 22, kv. 36; Roza Mitrofanovna Balitskaya, ulitsa Vyborgskaya, 4, kv. 6; Albert Fedorovich Sholin, Teply Stan, 1a mikroraion, korpus 18, kv. 100; Tatyana Borisovna Kasatkina, prospekt Mira, 120, kv. 226; Natalya Nikolaevna Kuznetsova, ulitsa Dnepropetrovskaya, 23, korpus 3, kv. 130, all of Moscow, U.S.S.R.

[21] Appl. No.: 616,946

[22] Filed: Sept. 26, 1975

[51] Int. Cl.² .................................................. C12B 1/00
[52] U.S. Cl. .................................... 195/47; 195/36 R; 195/112

[58] Field of Search ........................ 195/36 R, 47, 112

[56] References Cited

U.S. PATENT DOCUMENTS

| 3,002,889 | 10/1961 | Kinoshita et al. | 195/47 |
| 3,254,002 | 5/1966 | Megna et al. | 195/47 |

*Primary Examiner*—R. B. Penland
*Attorney, Agent, or Firm*—Steinberg & Blake

[57] ABSTRACT

The method of preparing L-glutamic acid and its sodium salt by growing, on a nutrient medium containing sources of nitrogen, carbon and mineral salts a strain producent of L-glutamic acid, *Micrococcus glutamicus* "VNIIgenetika" 3144, obtained from the strain *Micrococcus glutamicus* "VNIIGenetika" 490 by multi-step selection with mutagenic factors-diethyl sulphate and ultra-violet radiation— the biotin concentration in the liquid mineral medium preferably being such as to ensure the maximum yield of L-glutamic acid.

4 Claims, No Drawings

METHOD OF PREPARING L-GLUTAMIC ACID AND ITS SODIUM SALT

This invention relates to the method of preparing L-glutamic acid and its sodium salt which are used in medicinal and food industries.

There exists in the prior art a method for preparing L-glutamic acid and its salts by microbiological processes. Strain *Micrococcus glutamicus* "VNIIGenetika" 490 is used in this process to produce glutamic acid on high-biotin molasses media. While biotin inhibits production of glutamic acid by other known strains, in the known method biotin concentration in mineral media containing glucose is as high as 7.5 mcg/liter, this concentration ensuring the maximum synthesis of glutamic acid. VNIIGenetika is the Russian abreviation in English of the Institute — "All Union Institute of Genetics and Selection of Industrial Microorganisms." The productivity of *Micrococcus glutamicus* "VNIIGenetika" 490 grown on molasses media and containing from 15 to 20 mcg of biotin per liter, is about 40 g of L-glutamic acid per liter. The strain synthesizes $11.3 \times 10^9$ cells in a milliliter of the medium. The productivity per cell is $1.0 \times 10^{-9}$ mg of L-glutamic acid. The strain is grown for 60-65 hours; the quantity of dissolved oxygen at which the yield of L-glutamic acid is maximum, is 3.8 g/liter per hour$^{-1}$. On the termination of the fermentation process, the culture fluid is treated with calcium oxide, taken in the quantity of 1.5-2 percent by weight, then heated to boiling, and the formed precipitate of the biomass and calcium hydroxide is separated on a filter. The alkaline filtrate is neutralized with orthophosporic acid and the obtained calcium phosphate precipitate is separated again. The filtrate is passed through a column packed with a clarifying condensation type macroporous resin on the basis of metaphenylene diamine, formaldehyde and phenol, to remove coloured compounds.

The resin practically adsorbs no mineral salts or glutamic acid, but possesses a high adsorbing power with respect to coloured compounds contained in the culture filtrate.

The clarified filtrate is condensed by evaporation, acidified to pH 3.2, and crystalline L-glutamic acid is isolated. The yield of L-glutamic acid is 84 per cent by weight.

The disadvantage inherent in the known method is complexity of the process which is due to the fact that two filtration steps are required to separate glutamic acid from suspended substances, each filtration step being connected with inevitable loss of the solution together with moist precipitate. Moreover, treatment of the culture fluid with calcium oxide with heating produces additional quantities of coloured compound on account of condensation of amino acids and carbohydrates contained in the solution in the conditions of strongly alkaline medium. Furthermore, the known method employs strain *Micrococcus glutamicus* "VNIIGenetika " 490 that has relatively low resistance toward the inhibiting action of biotin. The strain produces ample mass and requires intense aeration during the synthesis of L-glutamic acid. This strain has low productivity per cell and the fermentation process takes relatively much time.

The object of this invention is to improve the resistance of the synthesis of L-glutamic acid to the inhibiting action of biotin.

Another object is to increase the productivity per cell and to decrease the time of the fermentation process.

Still another object of the invention is to increase the yield of the end product and to simplify the process as a whole.

The objects have been attained by a method for preparing L-glutamic acid and its sodium salt by cultivating *Micrococcus glutamicus* with aeration on a culture medium containing sources of carbon, nitrogen, and mineral salts, treating the culture fluid to precipitate the propagated mass, removing coloured admixtures, evaporating the obtained solution, acidifying this solution of pH 3.0-3.2 with subsequent isolation of the end product, using according to the invention, strain *Micrococcus glutamicus* "VNIIGenetika" 3144 selected from the strain *Micrococcus glutamicus* "VNIIGenetika" 490 by multi-step selection with mutagenic factors—diethyl sulphate and ultra-violet radiation—and characterized by the following morpholgical and physiological properties: when grown on agar meat-peptone medium for 5 days, at 28° C, it forms round, bright orange colonies, 3-5 mm in diameter, the cells are elongated 1.8 mc. On synthetic Glover's medium containing 20 mcg/liter of biotin, grown for 5 days at 28° C, it forms round, smooth, creamy colonies 1.5-2 mm in diameter. When grown on organic and mineral agar media it does not forms colonies at a temperature of 37° C. It does not thin gelatin. When grown on potato its growth is moderate, the colour bright yellow; it does not colour the medium; reduces nitrates into nitrites, possesses urease activity. Biotin concentration in liquid mineral medium, ensuring the maximum yield of glutamic acid, is 20 mcg/liter; the maximum cell concentration in the fermented broth is $3 \times 10^9$ (nutrient medium contains 20 percent by weight of molasses). The production of L-glutamic acid is about 40 g/liter. To precipitate the biomass, the culture fluid should be treated with orthophosphoric acid in the quantity 0.4-2 percent by weight with respect to the weight of the culture fluid (to pH 5-6) at a temperature of 60°-100° C.

The biomass can be precipitated also with calcium oxide taken in the quantity of 0.1-1 percent with respect to the weight of the culture fluid, with subsequent addition of orthophosphoric acid in the quantity of 0.4-2 percent with respect to the weight of the culture fluid (to pH 5-6) at a temperature of 60°-100° C.

The culture fluid can also be treated with calcium oxide in the quantity of 0.1-1.0 percent by weight, with the addition of hydrochloric acid in the quantity of 0.1-0.5 percent with respect to the weight of the culture fluid, with subsequent treatment with orthophosphoric acid in the quantity of 0.1-0.5 percent with respect to the weight of the culture fluid (to pH 5-6) at a temperature of 60°-100° C.

The proposed method is realized as follows.

The producent strain is *Micrococcus glutamicus* "VNIIGenetika" 3144 obtained by multi-step selection with mutagenic factors (diethyl sulphate vapour, ultraviolet radiation) from the starting strain *Micrococcus glutamicus* "VNIIGenetika" 490. The selection of strains was done on a medium containing 20 percent by weight of molasses. Strains possessing highest productivity were selected at each step.

The strain is characterized by the following morphological and physiological properties:

---

Hottinger Agar medium: after cultivation for five days at

| -continued | |
|---|---|
| (100 mg % of amine nitrogen) | 28° C the colonies are dense, round (3-5 mm in dia), smooth edge, smooth surface, or with 1-2 minor concentric folds; the center is elevated as a cone; colour - bright yellow. Streak (two-day cultivation at 28° C): growth moderate, smooth edge moist, gloss, smooth surface, flat profile, yellow colour. Cells elongated, 1.8 micron |
| Glover's synthetic medium containing 20 mcg of biotin per liter | Cells, elongated, 1.8 micron Colonies (five-day cultivation at 28° C) 1.5-2 mm in dia., round, smooth, glossy surface, cream colour. |
| Potato medium | Moderate growth, bright yellow colour; does not colour the medium. Does not thin gelatin. Does not change milk. Reduces nitrates to nitrites. |

Does not form colonies on agar media, both synthetic and mineral, at a temperature of 37° C.

Biotin concentration in a liquid mineral medium, ensuring the maximum yield of L-glutamic acid, is 20 mcg/liter.

The maximum cell concentration in the fermented broth (medium containing 20 percent of molasses) is $3 \times 10^9$.

The quantity of dissolved oxygen in g/liter per hour, that ensures the maximum yield of L-glutamic acid, with culture medium containing molasses, is 1.6 (in Erlenmeyer 250-ml flasks grown in 30 ml of media on reciprocating shakers, 220-240 rpm).

The length of the fermentation of said strain depends on the aeration conditions, namely: at a rate of oxygen dissolution of 2.4 g/liter × hour$^{-1}$, the fermentation process continues for 35 hours; at 5.4 g/liter × hour$^{-1}$–30 hours; at 7.0 g/liter × hour$^{-1}$–25 hours.

The inoculum is grown as follows.

One-day-old culture of said strain, grown on slant Hottinger agar is used to inoculate nutrient medium having the following composition, in percent by weight:

| molasses | 0.8 | MgSO$_4$ . 7H$_2$O | 0.03 |
|---|---|---|---|
| NH$_4$Cl | 0.5 | CaCO$_3$ | 1.0 |
| corn steep liquor | 0.3 | water | to 100 |
| K$_2$HPO$_4$ | 0.05 | | |

The pH of the medium is adjusted with NaOH to 7.2.

The inoculum is grown in flasks with constant stirring for 16 hours and then used to inoculate fermentation medium having the following composition, in percent by weight:

| KH$_2$PO$_4$ | 0.5 | urea | | 1.2 |
|---|---|---|---|---|
| MgSO$_4$ . 7H$_2$O | 0.3 | molasses | | 20 |
| CaCO$_3$ | 1.0 | tap water | to make | 100 |

The quantity of the inoculum is 2.5 percent by weight.

Urea is sterilized separately from the other components of the fermentation medium, in the form of a 40 percent solution, and is added to the medium before inoculation.

The fermentation is carried out at a temperature of 28°-30° C with continuous agitation and aeration for 25-35 hours.

The obtained culture fluid is heated to a temperature of 50° C.

To the hot culture fluid containing to 40 g/liter of L-glutamic acid, concentrated (73 percent) orthophosphoric acid is added in the quantity of 0.4-2 percent with respect to the weight of the culture fluid (the pH of the medium should be 5-6) to precipitate biomass and other suspended substances. Orthophosphoric acid reacts with calcium and magnesium cations contained in the culture fluid to form a precipitate that is co-precipitated with microbial cells and then separated by filtration. Since calcium ion concentration in the culture fluid depends on the degree of calcium carbonate dissolution and can vary with various batches, the effect of these changes can be removed by adding 0.1-1.0 percent by weight of calcium oxide before adding orthophosphoric acid to the culture fluid. In this case, quick-lime or slaked lime should be added to the hot culture fluid in the quantity of 0.1-1 percent by weight (calculating with reference to calcium oxide). The fluid is stirred for 5-15 minutes and concentrated (73 percent) orthophosphoric acid is added with stirring in the quantity of 0.1-0.5 percent of the weight of the culture fluid, so that the final pH should be 5-6. The solution is heated to 70°-100° C, filtered under pressure through culico or belting fabric, the precipitate on the filter is washed with water (10 percent of the volume of the filtered solution) and blown with air. The washings are added to the filtrate.

The culture filtrate is passed through an ion-exchange column. The first portions of the solution (displaced water) emerging from the column are discarded, and the clarified solution containing L-glutamic acid is collected. The remaining quantities of the solution are displaced from the column with water acidified to pH 5 and added to the clarified solution. The optical density of thus treated solution should be 0.06-0.07 ($\lambda = 535$ nm, 2 = 10 mm).

The ion exchange resin is recovered by passing two volumes (with respect to the resin volume) of alkaline solution containing 2 percent of NaOH and 2 percent of NH$_3$ (by weight). The resin is washed off the alkali (to pH 11 at the exit from the column), then a volume of a 1 percent hydrochloric acid is passed. The resin is finally washed with two volumes of water (the pH of the washings at the exit from the column is 2.5) and the column is ready for another clarification cycle.

The clarified solution is evaporated in vacuum at a temperature of 55° C, then hydrochloric acid is added to adjust the pH to 3.0-3.2, the solution is cooled to 10° C and kept for 20 hours with slowly stirring the solution. Crystals of L-glutamic acid are precipitated, separated by filtration, and washed.

The sodium salt of L-glutamic acid is obtained by procesing the aqueous solution of the acid with sodium hydroxide.

The yield of L-glutamic acid is to 86 percent by weight.

The proposed method employs the new strain *Micrococcus glutamicus* "VNIIGenetiak" 3144 differing from the known strain by some valuable properties that produce a significant effect on the fermentation process and isolation of L-glutamic acid, namely:

1. the resistance of the synthesis of L-glutamic acid to the inhibiting action of biotin increases three times;
2. the concentration of cells in a unit volume of the culture fluid decreases three times;
3. the precipitate of the biomass can be easily separated by filtration;
4. the productivity of a cell increases six times;

5. L-glutamic acid is intensively synthesized at a lower (three times less) concentration of dissolved oxygen in the nutrient medium;

6. The fermentation process is continued for a period of time 30-35 hours less than in the known process.

The proposed method simplifies the process by decreasing the number of labour-consuming operations connected with filtration of solutions at the stage of preliminary processing of the culture fluid, and decreases the loss of L-glutamic acid in these operations.

The biomass precipitate obtained in the preliminary processing of the culture fluid can be dried and utilized as fodder containing to 45 percent of microbial mass and 55 percent of calcium phosphate.

For a better understanding of the present invention, the following Examples of its practical embodiment are given by way of illustration.

EXAMPLE 1

One-day-old culture of *Micrococcus glutamicus* "VNIIGenetika" 3144, grown on Hottinger slant agar, is used to inoculate the seeding culture medium in 750 ml flasks. The quantity of the nutrient medium is 75 ml, and it has the following composition, in percent by weight:

| molasses | 8 | $K_2HPO_4$ | 0.05 |
|---|---|---|---|
| $NH_4Cl$ | 0.5 | $MgSO_4 \cdot 7H_2O$ | 0.03 |
| corn steep liquor | 0.3 | $CaCO_3$ | 1.0 |
| water to make 100. | | | |

The pH of the medium is adjusted with a 60 percent solution of NaOH to 7.2. The medium is sterilized for thirty minutes at 0.8 atm. The seeding material is grown for 15-17 hours on a reciprocating shaker (220-240 rpm).

The seeding material (75 ml) is transferred into a 5-liter fermentation vessel containing three liters of nutrient medium of the following composition, in percent by weight:

| molasses | 20 | urea | | 0.8 |
|---|---|---|---|---|
| $KH_2PO_4$ | 0.5 | $CaCl_3$ | 1.0 | |
| $MgSO_4 \cdot 7H_2O$ | 0.3 | water | to make | 100 |

The pH of the medium 6.8-7.0

The fermentation medium (without urea) is sterilized in the fermentation vessel at a temperature of 124°-1126° C for an hour, and then coold to 30° C.

Urea, a 40 percent solution in water, is sterilized separately in an autoclave at 0.5 atm for 30 minutes and added to the medium immediately before inolucation.

The fermentation process is effected at a temperature of 30° C with continuous stirring (700 rpm) and aeration (0.8 volume of air per volume of medium per minute). The sulphite value 2.4 g $O_2$/liter/hour. As the pH of the medium falls below 7.0, a 40 percent solution of urea is automatically added. In 35-hour fermentation, 37 g/liter of L-glutamic acid are accumulated in the culture fluid.

The specific gravity of the culture fluid is 1.05; the refractive index 1.3600; the pH 6.8. Its 1 liter, containing 37 g of L-glutamic acid, is heated to 50° C and calcium oxide is added in the quantity of 5 g per liter. The fluid is stirred for 10 minutes, and then concentrated (73 percent) orthophosphoric acid is added gradually with stirring to adjust the pH to 5.5. The solution is heated to 80° C for 10 minutes, then cooled to 70° C, and filtered under pressure through calico and belting fabric. The precipitate is washed with 100 ml of water and the washings are added to the main filtrate.

The optical density of the filtrate D is 2, $\lambda = 10$ mm, 535 nm.

The filtrate is passed through an ion-exchange column packed with 200 ml of macroporous condensation type resin on the basis of methaphenylene diamine, formaldehyde, and phenol (resorcinol) at a rate of 200 ml per hour. The first 70-ml portion of the solution, that emerges from the column, is discarded. The next portions of the solution containing L-glutamic acid, are collected together with the residual portion of the starting solution, that is displaced from the column with 300 ml of water acidified to pH 5 with hydrochloric acid.

The clarified solution is evaporated in vacuum at a temperature of 55° C to the residual volume of 200 ml.

Concentrated hydrochloric acid is added with stirring to the evaporated solution to adjust the pH to 3.2. The solution is now cooled in a crystallization vessel to 10° C and kept for 20 hours with slowly stirring. The precipitated crystals are separated on a filter, washed with water acidified to pH 3.2 with hydrochloric acid, and dried.

The yield of L-glutamic acid is 31.45 g (85 percent). The assay is 98 percent.

EXAMPLE 2

The producent strain, the composition of the inoculum and fermentation medium, and also their preparation, are the same as in Example 1. The difference is that the stirrer operates at a speed of 1300 rpm (in the fermentation vessel), and the aeration rate is 1 volume of air per volume of the medium per minute (the sulphite value 7 g $O_2$/liter/hour). The fermentation is continued for 25 hours. The yield of L-glutamic acid is 36 g/liter.

A liter of the culture fluid, heated to a temperature of 50° C is mixed with 7 g of calcium oxide. In 10 minutes, orthophosphoric acid (73 percent) is added gradually with stirring to adjust the pH of the medium to 6. The fluid is heated to a temperature of 70° C, kept at this temperature for 15 minutes, and filtered under pressure through calico and belting fabric. The precipitate on the filter is washed with 100 ml of water. The obtained filtrate is then clarified on an ion-exchange column, evaporated, the acid is crystallized, and processed as described in Example 1. To the obtained crystal of L-glutamic acid added are 60 ml of water and a 50 percent solution of sodium hydroxide to pH 6.9. The solution is heated to 80° C, kept at this temperature for 20 minutes with stirring, and filtered hot through a bed of activated carbon (2 g) on the filter. The obtained filtrate is evaporated and crystallized to prepare 27 g (75 percent by weight) of monosodium glutamate monohydrate.

EXAMPLE 3

The fermentation process is the same as in Example 1.

To 1 liter of the culture filtrate containing 37 g of L-glutamic acid, heated to 50° C, added with stirring are 7 g of calcium oxide in 30 ml of water. The stirring is continued for 10 minutes, and 4 ml of concentrated hydrocloric acid and orthophosphoric acid are then added to adjust the pH of the medium to 6. The fluid is heated to a temperature of 100° C, then cooled to a temperature of 70° C and filtered as described in Example 1. The obtained filtrate is clarified, evaporated, and L-glutamic acid is crystallized as described in Example 1. The yield of L-glutamic acid is 32 g, i.e. 86.4 percent by weight.

We claim:

1. A method of preparing L-glutamic acid and its sodium salt which comprises cultivating on a nutrient medium containing sources of carbon, nitrogen, and mineral salts *Micrococcus glutamicus*"VNIIGenetika" 3144, obtained from strain *Micrococcus glutamicus* "VNIIGenetika" 490 by multistep selection with mutagenic factors diethyl sulphate and ultra-violet radiation, precipitating the resulting biomass and recovering L-glutamic acid therefrom.

2. A method according to claim 1, in which in order to precipitate the propagated biomass, the culture fluid is treated with orthophosphoric acid in the quantity of 0.4–2 percent by weight with respect to the culture fluid to adjust the pH of the medium to 5–6, at a temperature of 60°–100° C.

3. A method according to claim 1, in which, in order to precipitate the propagated biomass, the culture fluid is treated with calcium oxide in the quantity of 0.1–1 percent by weight with respect to the culture fluid with subsequent addition of orthophosphoric acid in the quantity of 0.4–2 percent by weight with respect to the culture fluid, to adjust the pH of the medium to 5–6, at a temperature of 60°–100° C.

4. A method according to claim 1, in which, in order to precipitate the propagated biomass, the culture fluid is treated with calcium oxide in the quantity of 0.1–1.0 percent by weight with respect to the culture fluid, then hydrochloric acid is added in the quantity of 0.1–0.5 percent by weight with respect to the culture fluid, with subsequent treatment with orthophosphoric acid in the quantity of 0.1–0.5 percent by weight with respect to the culture fluid to adjust the pH of the medium to 5–6, at a temperature of 60°–100° C.

* * * * *